ically, US010344881B2

United States Patent
Alvarez et al.

(10) Patent No.: US 10,344,881 B2
(45) Date of Patent: Jul. 9, 2019

(54) APPARATUS AND METHOD FOR A VALVE FIXATION

(71) Applicant: FLUID AUTOMATION SYSTEMS S.A., Versoix (CH)

(72) Inventors: Raphael Alvarez, Nyon (CH); Christophe Bertrand, Chateleine (CH); Vincent Tanari, Satigny (CH); Pierre Sirdey, Geneva (CH)

(73) Assignee: Fluid Automation Systems S.A., Versoix (CH)

( * ) Notice: Subject to any disclaimer, the term of this patent is extended or adjusted under 35 U.S.C. 154(b) by 0 days.

(21) Appl. No.: 15/113,346

(22) PCT Filed: Feb. 5, 2015

(86) PCT No.: PCT/EP2015/052414
§ 371 (c)(1),
(2) Date: Jul. 21, 2016

(87) PCT Pub. No.: WO2015/118070
PCT Pub. Date: Aug. 13, 2015

(65) Prior Publication Data
US 2017/0023144 A1    Jan. 26, 2017

Related U.S. Application Data

(60) Provisional application No. 61/936,156, filed on Feb. 5, 2014.

(51) Int. Cl.
*F16K 27/00* (2006.01)
*A61M 39/22* (2006.01)
*F15B 13/08* (2006.01)

(52) U.S. Cl.
CPC .......... *F16K 27/00* (2013.01); *A61M 39/223* (2013.01); *F15B 13/0821* (2013.01);
(Continued)

(58) Field of Classification Search
None
See application file for complete search history.

(56) References Cited

U.S. PATENT DOCUMENTS 3,972,505 A * 8/1976 Padula ................ F16K 31/0627
137/625.65
4,051,861 A * 10/1977 Ellison ................ F15B 13/0814
137/15.09

(Continued)

FOREIGN PATENT DOCUMENTS

| DE | 19951662 A1 | 4/2000 |
| JP | 2007292217 A | 11/2007 |
| WO | 0106160 A1 | 1/2001 |

*Primary Examiner* — John Fox
(74) *Attorney, Agent, or Firm* — The Ollila Law Group LLC

(57) ABSTRACT

Devices and a method are described herein for fixing a valve to a base via a single point on the base. The valve may be fixed to the base using a plate inserted through a slot in the base and along a face of the valve body. The plate may include a head at one end to retain the plate in the slot. A valve may also be fixed to a base using a combination of a brace and a screw that threads into the base. The brace may include a lip that fits into a grove on the shaft of the screw. The valve body may include a lip to retain the combined screw and brace when the screw is not threaded into the base.

14 Claims, 5 Drawing Sheets

(52) U.S. Cl.
CPC ........ *F15B 13/0839* (2013.01); *F16K 27/003* (2013.01); *Y10T 137/87885* (2015.04)

(56) References Cited

U.S. PATENT DOCUMENTS

| | | | | |
|---|---|---|---|---|
| 4,493,476 | A | | 1/1985 | Strickland et al. |
| 4,735,230 | A | * | 4/1988 | Detloff ...................... E03D 1/00 137/15.26 |
| 4,817,670 | A | * | 4/1989 | Gogel ................. F15B 13/0817 137/269 |
| 6,371,166 | B1 | * | 4/2002 | Yoshizawa ............ B60T 8/3675 137/884 |
| 6,874,537 | B2 | * | 4/2005 | Hayashi .............. F15B 13/0814 137/269 |
| 7,216,843 | B2 | * | 5/2007 | Fukano ............... F15B 13/0814 251/129.01 |
| 2001/0029987 | A1 | * | 10/2001 | Rondreux ........... F15B 13/0807 137/883 |

* cited by examiner

APPARATUS AND METHOD FOR A VALVE FIXATION

BACKGROUND

1. Field of the Invention

The Application is related to the fields of valves, and more particularly, to fixing valves.

2. Description of the Prior Art

There is an increased need for fluid handling devices that are smaller in size. Fluid handling systems are necessary for applications such as medical instrumentation and manufacturing. In order for a fluid handling device to be effective and efficient, it should be simple, reliable, easy to assemble, and inexpensive. In many applications, it is desirable to decrease the number of components used in a valve fixing system to reduce costs and complexity.

Miniature valves, or valves that are less than 10 cm in size, are increasingly in use in fluid handling systems. Miniature valves may be actuated by a solenoid, a shape memory alloy, or any other type of actuator. Miniature valves often have small plastic parts that can be damaged when assembled to other parts.

Fixing a miniature valve to another component such as a manifold or a second valve often presents a challenge. The use of standard size screws to fix a miniature valve can cause problems because the screws may be proportionately quite large with respect to the valve. For example, using two standard sized screws to fix a miniature valve may require that the valve be larger in size to avoid losing performance. Using a single standard screw is also difficult because it may not be possible to apply enough force to avoid a leak without damaging plastic parts on a valve. Using smaller screws adds complication because it may be harder to tap the valve for the screw threads. Assembling a system that uses smaller screws is also difficult due to the challenge of aligning the screws before they are tightened and the ability for the screws to become lost.

What is needed is an improved method for fixing a valve that does not require excess space on a valve to implement, allows for the use of larger screws, is able to seal the valve without damaging parts, is easy to manufacture, and is easy to use in assembly/disassembly.

SUMMARY OF THE APPLICATION

According to an embodiment of the Application, a valve assembly includes a valve body, a base, and a first fixation device. The first fixation device fixes the valve body to the base via a single location on the base.

According to an embodiment of the Application, a valve fixing device for fixing a valve body to a base includes a brace and a screw. The screw is configured to fasten the brace against the valve body.

According to an embodiment of the Application, a method for fixing a valve body to a base includes the steps of fixing the valve body to the base via a single location on the base using a first fixation device.

ASPECTS OF THE APPLICATION

Preferably, the first fixation device is a plate.
Preferably, the single location on the base is a slot, and the plate is configured to be inserted into the slot so that the plate pulls the base towards an interface between the valve body and the base.

Preferably, the plate is configured to rest on a face of valve body opposite the interface so that the plate pushes the valve body towards the interface between the valve body and the base.

Preferably, the valve body includes a channel on the face of the valve body opposite the interface, and the channel is configured to seat the plate, allowing the plate to push the valve body towards the interface between the valve body and the base.

Preferably, the plate has a head.
Preferably, the valve assembly further comprises a bend configured to rest outside the base when the plate is fully inserted into the valve assembly.

Preferably, the valve assembly further comprises a brace, wherein the first fixation device is configured to fasten a first location of the brace against the valve body, and a second location of the brace is configured to apply pressure to the first fixation device.

Preferably, the first fixation device is a screw.
Preferably, the second location of the brace is configured to apply pressure to the screw via a grove on the shaft of the screw.

Preferably, the brace includes a notch configured to fit into the grove of the first fixation device.

Preferably, the valve body is a miniature valve.
Preferably, the valve body (102) is a 3-way valve.
Preferably, the base is a manifold base.
Preferably, the screw includes a shaft having a notch, and wherein the brace includes a first side and a second side, the first side configured to rest on a face of the valve body opposite an interface between the valve body and the base, and the second side oriented substantially 90 degrees from the first side, and wherein the second side includes a notch configured to fit into the notch on the screw.

Preferably, the brace and the screw are configured to be retained by a lip on the valve body.

Preferably, the brace and the screw are configured to be retained by the lip on the valve body between the second side of the brace and the shaft of the screw.

Preferably, the first fixation device is a plate, and fixing the valve body to the base at the single location using the first fixation device further comprises the steps of inserting the plate through a slot located in the base and along a face of the valve body opposite an interface between the valve body and the base.

Preferably, the face of the valve body includes a channel configured to seat the plate.

Preferably, the channel on the face of the valve body opposite an interface between the valve body and the base is angled.

Preferably, the first fixation device is a screw, and fixing the valve body to the base at the single location using the first fixation device further comprises the steps of seating a notch of a brace into a grove located on a shaft of the screw; and fastening the brace against the valve body with the screw.
Preferably, the valve body includes a lip configured to retain the brace and the screw.

BRIEF DESCRIPTION OF THE DRAWINGS

The same reference number represents the same element on all drawings. It should be understood that the drawings are not necessarily to scale.

DETAILED DESCRIPTION OF THE APPLICATION

FIGS. 1-8 and the following description depict specific examples to teach those skilled in the art how to make and use the best mode of the Application. For the purpose of teaching inventive principles, some conventional aspects have been simplified or omitted. Those skilled in the art will appreciate variations from these examples that fall within the scope of the Application. Those skilled in the art will appreciate that the features described below can be combined in various ways to form multiple variations of the Application. As a result, the Application is not limited to the specific examples described below, but only by the claims and their equivalents.

Figure 1:
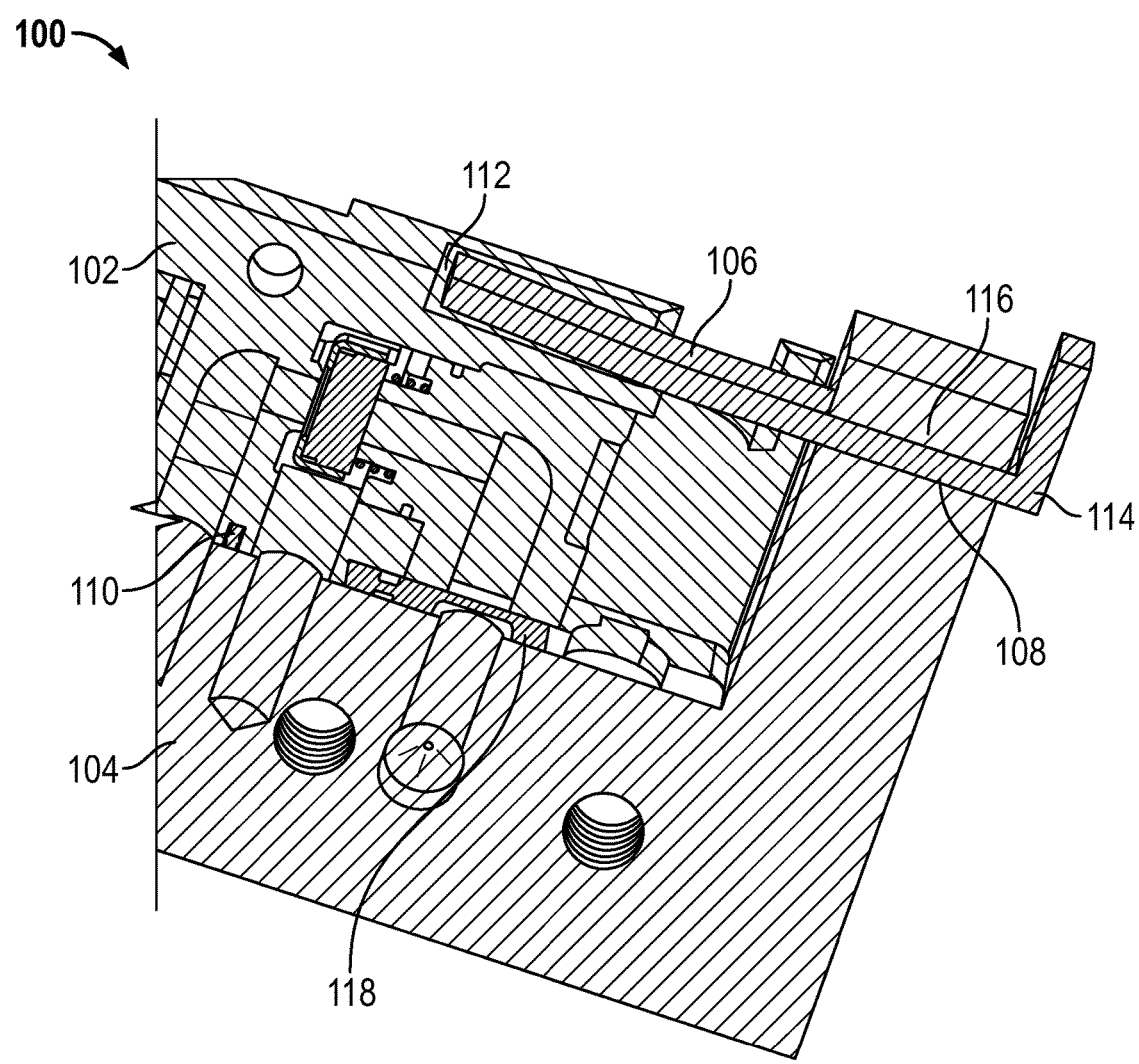
FIG. 1 shows a cross-sectional view of a valve assembly 100 according to an embodiment of the Application.

FIG. 1 shows a valve assembly 100 according to an embodiment of the Application. The valve assembly 100 is optimally arranged to be incorporated into a fluid handling system (not shown). Valve assembly 100 can be used in a variety of implementations, as may be understood by those in the art. For example, valve assembly 100 may include slices that are part of a bankable valve system. Valve assembly 100 can advantageously control the delivery of a fluid (liquid, gas, solids suspended in liquid or gas, or a combination thereof).

Valve assembly 100 includes a valve body 102, a base 104, a plate 106, a slot 108, an interface 110, a channel 112, a head 114, a single location on the base 116, and a seal 118. The valve may include any type of actuator, number of ports, or positions, as may be known to those skilled in the art. In an embodiment, valve body 102 may be a miniature valve. For example, valve body 102 may be a miniature solenoid 3-way valve. The base may be any component to which a valve body is typically affixed. For example, the base may be a manifold or a second valve, or a valve block. In the embodiment of FIG. 1, base 104 is a manifold. This is not intended to be limiting, however, as it is possible to fix valve body 102 to any object using the apparatuses and method described in the present Application.

In the embodiment of FIG. 1, base 104 is depicted as being in contact with two sides of valve body 102. It should be appreciated, however, that base 104 may be in contact with one or any number of sides of valve body 102. Valve assembly 100 includes an interface 110 between valve body 102 and base 104 that represents a barrier through which fluids may pass between the bodies. Interface 110 requires pressure to seal. For example, in FIG. 1 seal 118 seals a fluid passageway between valve body 102 and the manifold that is base 104.

Valve body 102 may be attached to base 104 via single location on the base 116 via a first fixation device. Single location on the base may be any feature of the base capable of accommodating a mechanical fastener. For example, the single location on the base may be a slot or a threaded hole. The first fixation device may be any type of mechanical fastener. For example, the first fixation device may be a fixation plate, a screw, a clamp, a rivet, a clip, a pin, or any other fastening device known to those in the art.

In the embodiment of FIG. 1, the first fixation device is fixation plate 106. Fixation plate 106 is a substantially flat plate having head 114 at one end. Fixing plate 106 may be inserted into the side of slot 108 opposite valve body 102. Plate 106 may take any form that includes at least one substantially flat section capable of being inserted into a slot. The plate may be made from metal or any other type of material. Fixing plate 106 may pass through the length of slot 108 and emerge adjacent valve body 102. Fixing plate 106 may then be inserted into channel 112 of valve body 102 to secure the assembly of valve body 102 and base 104. Channel 112 may include a slight incline, angling away from slot 108 opposite the direction of interface 110. The slight incline in channel 112 forces plate 106 to flex, which allows plate 106 to be further secured in place with greater tension.

In embodiments fixation plate 106 may include a head 114 opposite the insertion end of the plate. Head 114 may provide a graspable end that makes fixation plate 106 easy to handle when assembling valve assembly 100. In embodiments, head 114 may come to a rest outside of base 104 when plate 106 is fully inserted, further securing fixation plate 106 inside valve assembly 100. This is not intended to be limiting, however, as head 114 may come to rest on another portion of base 104, or head 114 may not come to a rest against any part of base 104. In the embodiment of FIG. 1, head 114 is a bend formed in fixation plate 106. However, other formats or shapes of head 114 are anticipated by this Application, as will be understood by those skilled in the art.

In the embodiment of FIG. 1, single location on the base 116 is slot 108. Slot 108 on base 104 is configured to receive fixing plate 106. In embodiments, slot 108 may be open on both sides or on only one side. At slot 108, fixing plate 106 may exert an upwards force on base 104, pulling base 104 towards interface 110 between valve body 102 and base 104. Valve body 102 may include channel 112. At channel 112, fixing plate 106 may apply a downward force pushing valve body 102 towards interface 110 between valve body 102 and base 104. In this way, interface 110 and seal 118 are squeezed between valve body 102 and base 104, providing a seal. In the embodiment of FIG. 1, it may be seen that plate 106 applies forces to valve body 102 and base 104 along different sections of the longitudinal length of plate 106.

In the example of valve assembly 100, valve body 102 includes channel 112 for seating a fixing plate. This is not intended to be limiting, however, as valve body 102 may include any type of seat for a plate, or none at all.

Figure 2:
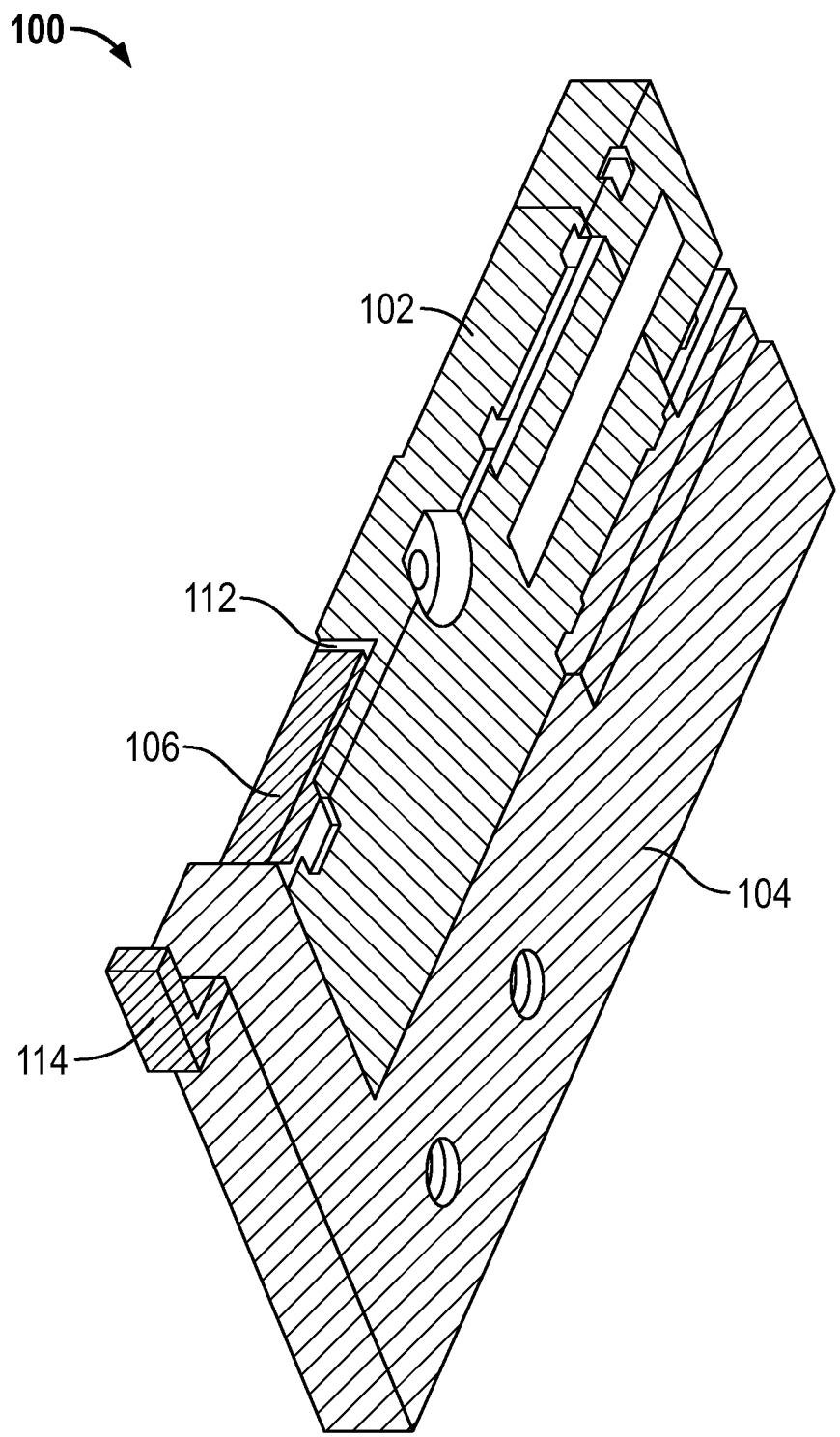
FIG. 2 shows a perspective view of a valve assembly 100 according to an embodiment of the Application.

FIG. 2 depicts a perspective view of valve assembly 100. In FIG. 2, a fully assembled valve assembly 100 may be viewed. It may be seen that valve body 102 is joined to base 104 via fixation plate 106. Fixation plate 106 is inserted through slot 108 (not shown) and channel 112 so that head 114 rests on an outside face of base 104.

Figure 3:
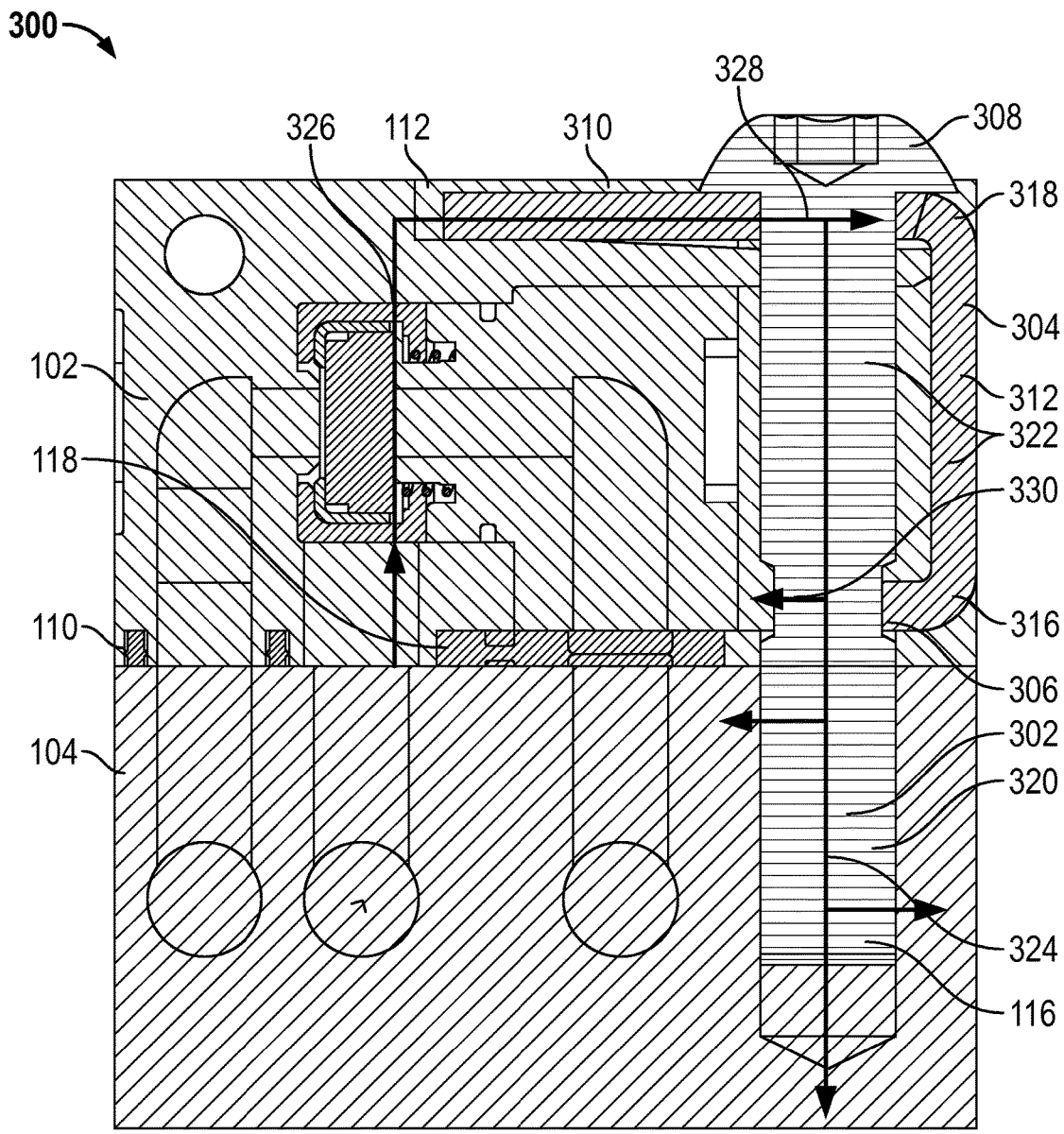
FIG. 3 shows a cross-sectional view of a valve assembly 300 according to an embodiment of the Application.

FIG. 3 depicts a cut-away view of a further embodiment of the application, valve assembly 300. Valve assembly 300 includes valve body 102, base 104, a screw 302, and a brace 304. Screw 302 includes a shaft 320, an annular notch 306, and a head 308. Brace 304 includes a first side 310, a second side 312, a notch 316, and bend 318. Bend 318 is located between first side 310 and second side 312 of brace 304.

Screw 302 fixes valve body 102 to base 104 with the help of brace 304. Screw 302 threads into base 104. The internal threads into which screw 302 tightens represent the single location on the base 116 used to fix valve body 102 to base 104.

Brace 304 may take any form wherein at least a portion of the brace may be fixed against the valve body. In the embodiment of FIG. 3, first side 310 and second side 312 of brace 304 are substantially straight segments. When fully fastened, first side 310 may come to rest on a face of valve body 102 that opposes interface 110. Head 308 of screw 302 may come to rest on the first side 310. In embodiments, screw 302 may thread through a hole in first side 310 of brace 304. In the example implementation of valve assembly 300, bend 318 is a rounded corner that makes a substantially 90 degree change between the orientation of first side 310 and second side 312 of brace 304. Second side 312 is oriented substantially parallel to shaft 320 of screw 302. On the end opposite bend 318, second side 312 terminates with notch 316. Notch 316 turns inward towards valve body 102 to form an inward protrusion.

Screw 302 includes a shaft 320 including a grove 306. When valve body 102 is fully fixed to base 104, grove 306 may be located inside valve assembly 300. Brace 304 may function as a cover for shaft 320 of screw 302.

Notch 316 of brace 304 is configured to fit into grove 306 of screw 302, to form a valve fixation device 322. In the embodiment of FIG. 3, grove 306 is annular in shape. This is not intended to be limiting, however. In embodiments, grove 306 may be a localized notch. In other embodiments, notch 316 of brace 304 may rest directly against shaft 320 of screw 302 with no grove.

Figure 4:
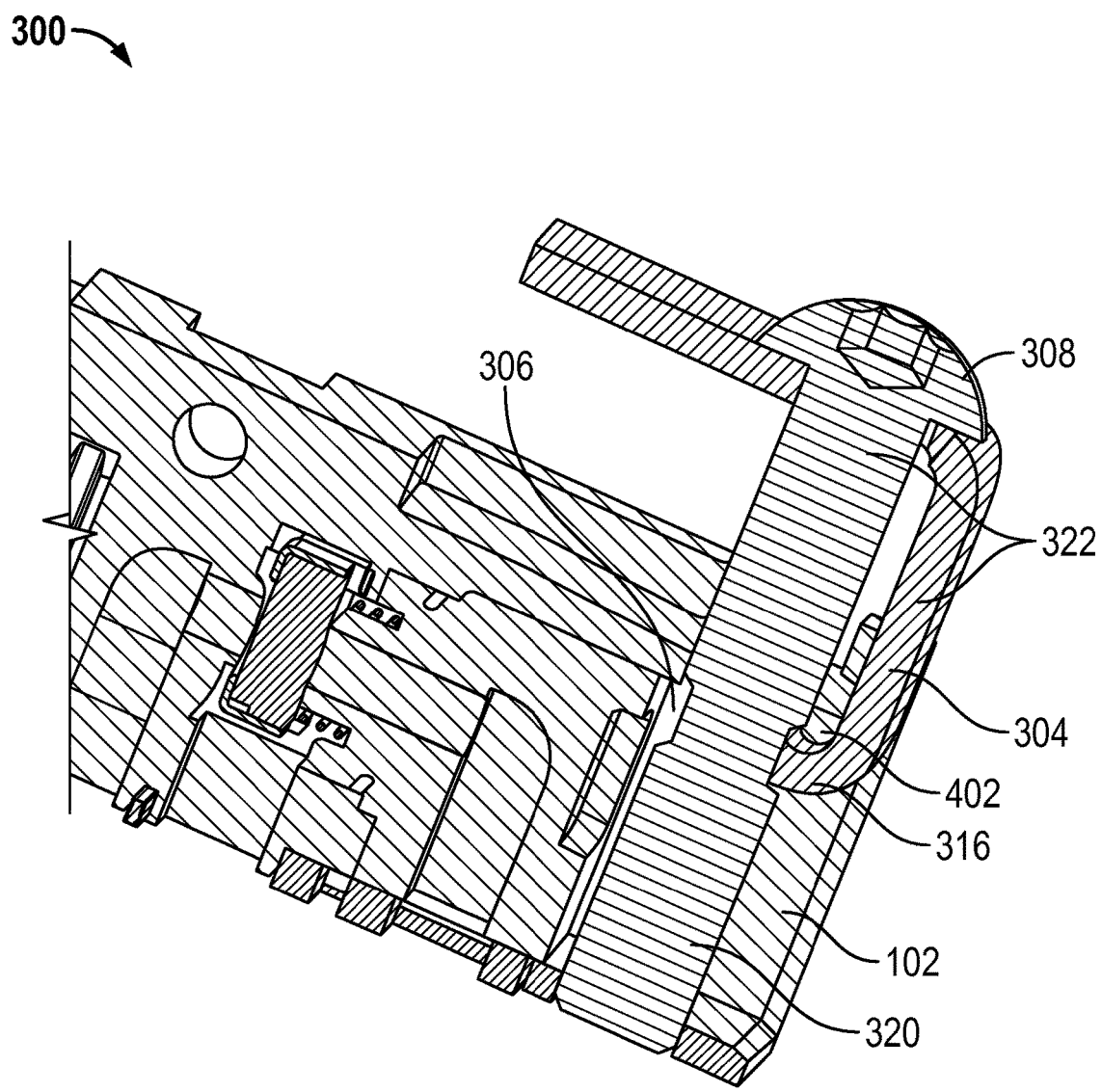
FIG. 4 shows a cross-sectional view of a valve assembly 300 according to an embodiment of the Application.

FIG. 4 depicts a cutaway view of valve fixation device 322 positioned in valve body 102. In FIG. 4, screw 302 of valve fixation device 322 is not threaded into base 104 (not pictured), but it is still retained by valve body 102. Screw 302 and brace 304 are in contact in two locations on valve fixation device 322. At a first location, the head 308 of screw 302 is in contact with a first side 310 of brace 304. At a second location, notch 316 of brace 304 is seated in grove 306 of screw 302. Between these two contact locations, an enclosed space is created between shaft 320 and brace 304. Valve body 102 further includes a lip 402, which is situated inside of the enclosed space created by valve fixation device 322. Lip 402 allows valve body 102 to retain valve fixation device 322 when screw 302 is not attached to base 104. Retaining valve fixation device 322 on valve body 102 makes the fixing of valve body 102 to base 104 much easier for the assembler because screw 302 and brace 304 are much less likely to be misaligned or to become lost.

Returning to FIG. 3, forces 324, 326, 328, and 330 may be seen. Valve fixation device 322 applies adequate sealing force on seal 118 and prevents leaks between valve body 102 and base 104. Force 324 represents the force into the manifold. Force 326 represents the seal and fluid pressure force. Force 328 represents the pressure that first side 310 of brace 304 applies to screw 302. Force 330 represents the pressure applied by notch 316 of brace 304 to screw 302.

Figure 5:
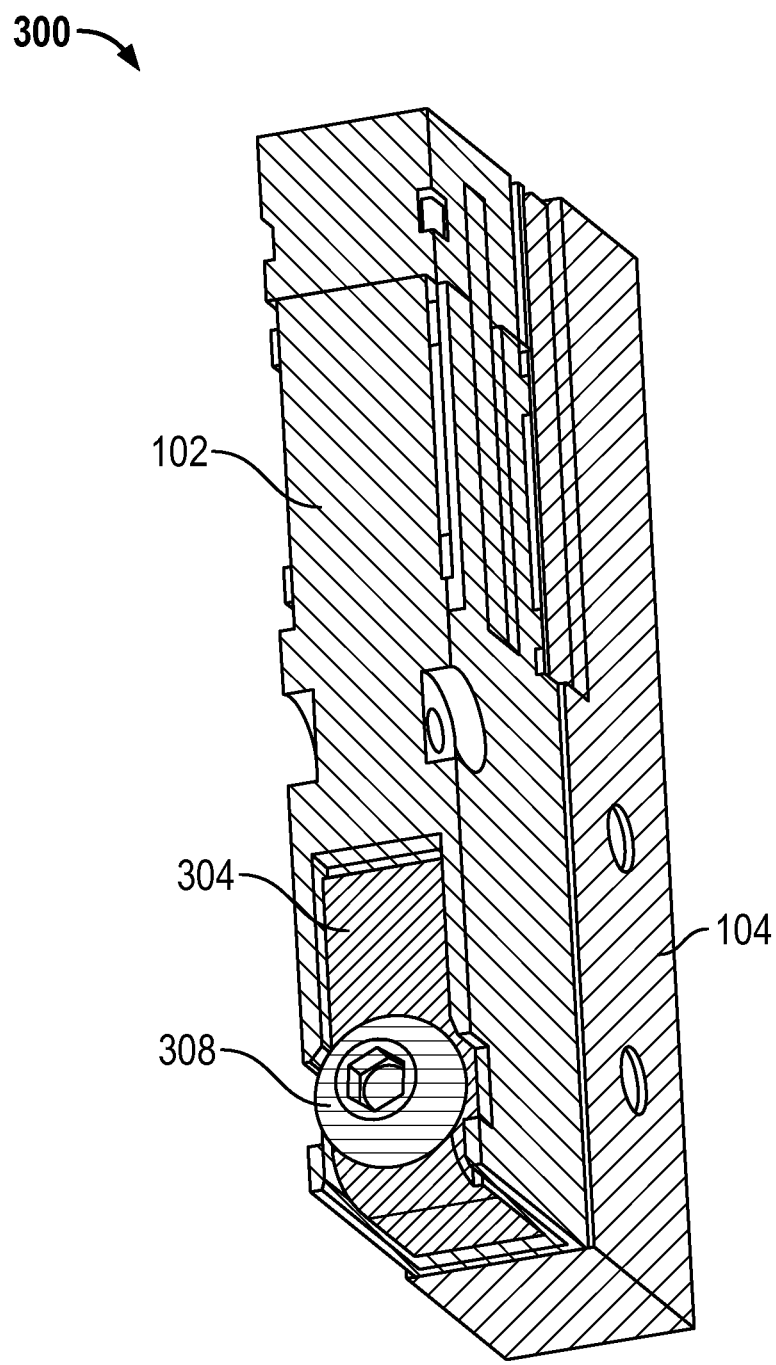
FIG. 5 shows a perspective view of a valve assembly 300 according to an embodiment of the Application.

FIG. 5 depicts a perspective view of valve assembly 300. In FIG. 5, valve body 102, base 104, brace 304, and screw head 308 may be seen fully assembled.

The various embodiments of the Application can be implemented to provide an apparatus and a method for fixing a valve that offers the advantage of attaching a valve to a base via a single point on the base. Accordingly, the valve including such fixing means is reliable, can be made smaller, is easier to manufacture, and is easier to assemble.

The detailed descriptions of the above embodiments are not exhaustive descriptions of all embodiments contemplated by the inventors to be within the scope of the Application. Indeed, persons skilled in the art will recognize that certain elements of the above-described embodiments may variously be combined or eliminated to create further embodiments, and such further embodiments fall within the scope and teachings of the Application. It will also be apparent to those of ordinary skill in the art that the above-described embodiments may be combined in whole or in part to create additional embodiments within the scope and teachings of the Application.

Thus, although specific embodiments of, and examples for, the Application are described herein for illustrative purposes, various equivalent modifications are possible within the scope of the Application, as those skilled in the relevant art will recognize. The teachings provided herein can be applied to other fluid control devices, and not just to the embodiments described above and shown in the accompanying figures. Accordingly, the scope of the Application should be determined from the following claims.

We claim:

1. A valve assembly (100) comprising:
    a valve body (102);
    a base (104);
    a first fixation device for fixing the valve body (102) to the base (104), wherein the first fixation device has a longitudinal axis and fixes the valve body (102) to the base (104) via a single location on the base (116); and
    a brace (304),
    wherein the first fixation device is configured to fasten a first location (310) of the brace (304) against the valve body (102) and a second location (316) of the brace (304) is configured to apply pressure (330) to the first fixation device in a direction transverse to the longitudinal axis, and wherein the first location (310) and the second location (316) are spaced apart along the longitudinal axis of the first fixation device.

2. The valve assembly (100) of claim 1, wherein the first fixation device is a screw (302).

3. The valve assembly (100) of claim 2, wherein the second location of the brace (304) is configured to apply pressure to the screw (302) via a groove (306) on the shaft (320) of the screw (302).

4. The valve assembly (100) of claim 3, wherein the brace (304) includes a notch (316) configured to fit into the groove (306) of the first fixation device.

5. The valve assembly (100) of claim 1, wherein the valve body (102) is a miniature valve.

6. The valve assembly (100) of claim 1, wherein the valve body (102) is a 3-way valve.

7. The valve assembly (100) of claim 1, wherein the base (104) is a manifold base.

8. A valve fixing device (322) for fixing a valve body (102) to a base (104), the valve fixing device (300) including:
    a brace (304); and
    a screw (302) having a longitudinal axis and configured to fasten the brace (304) against the valve body (102), wherein the screw threads into the base (104), wherein the screw (302) is configured to contact a first location of the brace (304) to fasten a first portion (310) of the brace (304) against the valve body (102), wherein a second location (316) of the brace (304) is configured to apply pressure (330) to the screw in a direction transverse to the longitudinal axis, wherein the first location (310) and the second location (316) are spaced apart along the longitudinal axis of the screw, and wherein the brace (304) comprises a bend (318) in the brace (304) positioned between the first location (310) and the second location (316).

9. The valve fixing device (322) of claim 8, wherein the screw (302) includes a shaft (320) having a notch (306), and wherein the brace (304) includes a first side (310) and a second side (312), the first side (310) configured to rest on a face of the valve body (102) opposite an interface (110) between the valve body (102) and the base (104), and the second side (312) oriented substantially 90 degrees from the first side (310), and wherein the second side (312) includes a notch (316) at the second location configured to fit into the notch (306) on the screw (302).

10. The valve fixing device (322) of claim 9, wherein the brace (304) and the screw (302) are configured to be retained by a lip (402) on the valve body (102).

11. The valve fixing device (322) of claim 10, wherein the brace (304) and the screw (302) are configured to be retained by the lip (402) on the valve body (102) between the second side (312) of the brace and the shaft (320) of the screw (302).

12. A method for fixing a valve body (102) to a base (104), comprising steps of:

fixing the valve body (102) to the base (104) via a single location (116) on the base using a first fixation device having a longitudinal axis by fastening a first location (310) of a brace (304) against the valve body (102) using the first fixation device; and applying pressure to the first fixation device in a direction transverse to the longitudinal axis with a second location (316) of the brace (304), the first location (310) and the second location (316) of the brace (304) being spaced apart along a longitudinal axis of the first fixation device.

13. The method of claim 12, wherein the first fixation device is a screw (302), wherein the second location of the brace (304) comprises a notch (316), and wherein fixing the valve body (102) to the base (104) at the single location (116) using the first fixation device further comprises the step of:

seating the notch (316) of the brace (304) into a groove (306) located on a shaft (320) of the screw (302).

14. The method of claim 13, wherein the valve body (102) includes a lip (402) configured to retain the brace (304) and the screw (302).

\* \* \* \* \*